United States Patent
Wang et al.

(10) Patent No.: US 12,048,816 B2
(45) Date of Patent: Jul. 30, 2024

(54) ANESTHESIA MACHINE EXHAUST EMISSION CONTROL SYSTEM AND CONTROL METHOD THEREFOR

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Sheng Wang, Shenzhen (CN); Dongsheng Liang, Shenzhen (CN); Caijin Luo, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 987 days.

(21) Appl. No.: 16/848,782

(22) Filed: Apr. 14, 2020

(65) Prior Publication Data
US 2020/0238042 A1    Jul. 30, 2020

Related U.S. Application Data

(63) Continuation of application No. PCT/CN2017/107054, filed on Oct. 20, 2017.

(51) Int. Cl.
*A61M 16/18* (2006.01)
*A61M 16/00* (2006.01)

(52) U.S. Cl.
CPC ........ *A61M 16/18* (2013.01); *A61M 16/0051* (2013.01); *A61M 16/009* (2013.01);
(Continued)

(58) Field of Classification Search
CPC .. A61M 16/0051; A61M 16/0087–009; A61M 16/01; A61M 16/021–022;
(Continued)

(56) References Cited

U.S. PATENT DOCUMENTS 6,622,726 B1    9/2003   Du
7,628,034 B2   12/2009   Berry et al.
(Continued)

FOREIGN PATENT DOCUMENTS

CN    2812964 Y      9/2006
CN    201533941 U    7/2010
(Continued)

OTHER PUBLICATIONS

International Search Report issued in corresponding International Application No. PCT/CN2017/107054, mailed Jul. 12, 2018, 4 pages.
(Continued)

*Primary Examiner* — Rachel T Sippel
(74) *Attorney, Agent, or Firm* — BAYES PLLC (57) ABSTRACT

An anesthesia machine exhaust emission control system detects a gas flow in a connection pipeline by an electronic flow detector and displays same by a display, and a controller controls, according to an operating state of the anesthesia machine, a switch so same turns on or turns off the connection pipeline. The method for controlling the connection exhaust emission control system comprises, directly displaying a gas flow value in the connection pipeline by the electronic flow detector, the controller and the display, so that the user can conveniently and accurately read the gas flow value in the connection pipeline. The connection pipeline is turned off when an anesthesia machine is in a standby status, thereby greatly saving exhaust gas recovery resources of a hospital.

20 Claims, 2 Drawing Sheets

(52) U.S. Cl.
CPC ... *A61M 16/022* (2017.08); *A61M 2016/0024* (2013.01); *A61M 2202/0241* (2013.01); *A61M 2205/3331* (2013.01); *A61M 2205/502* (2013.01)

(58) Field of Classification Search
CPC .. A61M 16/18–186; A61M 16/20–203; A61M 16/208–209; A61M 2016/0024; A61M 2016/0027–0033; A61M 2016/0241; A61M 2205/3331–3334; A61M 2205/3341
See application file for complete search history.

(56) References Cited

U.S. PATENT DOCUMENTS

| | | | |
|---|---|---|---|
| 2008/0190431 A1 | 8/2008 | Bellefeuille | |
| 2010/0078026 A1* | 4/2010 | Andrieux | A61M 16/0465 128/204.21 |
| 2012/0000549 A1 | 1/2012 | Thorne | |
| 2015/0147956 A1* | 5/2015 | Lindkvist | A61M 16/104 454/343 |
| 2018/0221606 A1* | 8/2018 | Brandt | A61M 16/0066 |

FOREIGN PATENT DOCUMENTS

| | | |
|---|---|---|
| CN | 2011100826 A1 | 8/2011 |
| CN | 202446626 U | 9/2012 |
| CN | 202724392 U | 2/2013 |
| CN | 203634604 U | 6/2014 |
| CN | 205598375 U | 9/2016 |
| GB | 2201098 A | 8/1988 |
| WO | 2017075656 A1 | 5/2017 |

OTHER PUBLICATIONS

First Office Action issued in related Chinese Application No. 201780094690.3, mailed May 23, 2022, 13 pages.
Extended European Search Report issued in related European Application No. 17929001.1, mailed Jul. 23, 2020, 6 bages.

* cited by examiner

ANESTHESIA MACHINE EXHAUST EMISSION CONTROL SYSTEM AND CONTROL METHOD THEREFOR

CROSS-REFERENCE TO RELATED APPLICATIONS

This application is a bypass continuation of PCT App. No. PCT/CN2017/107054 filed Oct. 20, 2017, for ANESTHESIA MACHINE EXHAUST EMISSION CONTROL SYSTEM, AND CONTROL METHOD THEREFOR, which is incorporated herein by reference in its entirety.

TECHNICAL FIELD

The present disclosure relates to the technical field of exhaust gas recovery, and in particular to an anesthesia machine exhaust emission control system and a control method therefor.

BACKGROUND

Anesthesia machine is an advanced medical device that may deliver various gases and volatile anesthetics, control and assist patient's breathing, and adjust patient's consciousness and pain level during an operation.

The anesthesia machine generates a certain amount of exhaust gas during use, and if the exhaust gas is directly discharged, it will cause damage to human health and the environment. Anesthesia gas scavenging system (AGSS) is a system for collecting exhaust gas discharged from an anesthesia machine, and this system is connected to a hospital exhaust gas recovery system and transfers the exhaust gas generated during the use of the anesthesia machine to the recovery system.

During the recovery of the exhaust gas generated by the anesthesia machine, a gas flow transferred from the gas scavenging system of the anesthesia machine to the hospital exhaust gas recovery system needs to be controlled within a certain range, and too high or too low gas flow will be hazardous to the patient's health. For the traditional gas scavenging system of the anesthesia machine, the gas flow transferred from the gas scavenging system of the anesthesia machine to the hospital exhaust gas recovery system is monitored by a mechanical float flowmeter, which has the problems of inconvenient observation and easy misreading of data. The hospital exhaust gas recovery system is usually connected to multiple anesthesia machines at the same time, and no exhaust gas is emitted when a single or several anesthesia machines are in a standby state. In order to ensure that all the anesthesia machines connected to the hospital exhaust gas recovery system work normally, the hospital exhaust gas recovery system will be in a continuous working state. At this time, the hospital exhaust gas recovery system extracts a large amount of air from the anesthesia machine in the standby state, causing waste of a hospital exhaust gas recovery resource.

SUMMARY

According to this, it is necessary to address the problems of inconvenient observation and easy misreading of data when the amount of exhaust emission of a traditional anesthesia gas scavenging system is monitored, and wasting of hospital exhaust gas recovery resources when the anesthesia machine is in standby, and provide an anesthesia machine exhaust emission control system and a control method therefor, which is easy to observe, has accurate readings, and saves on hospital exhaust gas recovery resources.

Disclosed is an anesthesia machine exhaust emission control system arranged between an exhaust gas recovery system and an anesthesia machine exhaust emission port, the anesthesia machine exhaust emission control system including:

a connection pipeline including a gas inlet end and a gas outlet end, wherein the gas inlet end of the connection pipeline is connected to the anesthesia machine exhaust emission port, the gas outlet end of the connection pipeline is connected to the exhaust gas recovery system, and exhaust gas generated by the anesthesia machine is capable of entering the exhaust gas recovery system through the connection pipeline;

an electronic flow detector arranged on the connection pipeline, wherein the electronic flow detector is capable of monitoring a gas flow in the connection pipeline;

a controller electrically connected to the electronic flow detector, wherein the controller is capable of obtaining a gas flow value in the connection pipeline that is monitored by the electronic flow detector;

a display electrically connected to the controller, wherein the controller is capable of transmitting the gas flow value in the connection pipeline to the display for display; and a switch, wherein the switch is arranged on the connection pipeline, the switch is capable of opening or closing the connection pipeline, the switch is electrically connected to the controller, wherein the controller is capable of controlling the switch according to an operating state of the anesthesia machine, when the anesthesia machine is in a ventilation state, the controller controls the switch to open the connection pipeline, and when the anesthesia machine is in a standby state, the controller controls the switch to close the connection pipeline.

In one of the embodiments, the anesthesia machine exhaust emission control system further includes an alarm, wherein the alarm is electrically connected to the controller; the controller is capable of comparing the gas flow value in the connection pipeline with a preset range value; and when the gas flow value in the connection pipeline overflows the preset range value, the controller controls the alarm to send out an alarm signal.

In one of the embodiments, the controller is capable of further controlling the switch according to the on-off state of the anesthesia machine; and when the anesthesia machine is in a power-off state, the controller controls the switch to close the connection pipeline.

In one of the embodiments, the anesthesia machine exhaust emission control system further includes a flow regulator, wherein the flow regulator is capable of adjusting the gas flow in the connection pipeline.

In one of the embodiments, the flow regulator is electrically connected to the controller; the controller is capable of comparing the gas flow value in the connection pipeline with a preset range value; when the gas flow value in the connection pipeline is greater than the maximum value of the preset range value, the controller controls the flow regulator to reduce the flow value allowed to pass through the flow regulator; and when the gas flow value in the connection pipeline is less than the minimum value of the preset range value, the controller controls the flow regulator to increase the flow value allowed to pass through the flow regulator.

In one of the embodiments, the anesthesia machine exhaust emission control system further includes an overflow unit, wherein the overflow unit is in communication with one end of the connection pipeline which is close to the anesthesia machine exhaust emission port; and when the amount of exhaust gas actually discharged from the anesthesia machine is greater than a gas extraction flow of the exhaust gas recovery system, excess exhaust gas is discharged from the overflow unit.

In one of the embodiments, the anesthesia machine exhaust emission control system further includes a replenishment unit, wherein the replenishment unit is in communication with one end of the connection pipeline which is close to the anesthesia machine exhaust emission port; and when the amount of exhaust gas actually discharged from the anesthesia machine is less than a gas extraction flow of the exhaust gas recovery system, gas in the environment is capable of entering the connection pipeline from the replenishment unit.

Also disclosed is an anesthesia machine exhaust emission control method, including:
obtaining an exhaust emission flow of the anesthesia machine;
displaying the exhaust emission flow of the anesthesia machine; and
obtaining an operating state of the anesthesia machine, and opening or closing an exhaust passage between an anesthesia machine exhaust emission port and an exhaust gas recovery system according to the operating state of the anesthesia machine, wherein when the anesthesia machine is in a ventilation state, the exhaust passage between the anesthesia machine exhaust emission port and the exhaust gas recovery system is opened; and when the anesthesia machine is in a standby state, the exhaust passage between the anesthesia machine exhaust emission port and the exhaust gas recovery system is closed.

In one of the embodiments, the anesthesia machine exhaust emission control method further includes:
comparing the obtained exhaust emission flow of the anesthesia machine with a preset range value; and
if the exhaust emission flow of the anesthesia machine is greater than the maximum value of the preset range value or less than the minimum value of the preset range value, sending out an alarm signal by an alarm.

In one of the embodiments, the anesthesia machine exhaust emission control method further includes:
obtaining the on-off state of the anesthesia machine; and
if the anesthesia machine is in a power-off state, closing the exhaust passage between the anesthesia machine and the exhaust gas recovery system.

According to the above-mentioned anesthesia machine exhaust emission control system and the control method therefor, the gas flow value in the connection pipeline is directly displayed by the electronic flow detector, the controller and the display; a user may conveniently know the gas flow value in the connection pipeline; and the display directly displays the gas flow value in the connection pipeline, which greatly improves the accuracy of data read by the user and ensures the smooth progress of an anesthesia process to a certain extent. At the same time, the controller controls the switch to open or close the connection pipeline according to the operating state of the anesthesia machine; and when a single or several anesthesia machines are in a standby state, the controller controls the switch to close the corresponding connection pipeline, and the hospital exhaust gas recovery system only needs to extract exhaust gas from the anesthesia machine which is discharging the exhaust gas, thereby greatly saving on the hospital exhaust gas recovery resource.

In the figures:
100—Anesthesia machine exhaust emission port
200—Anesthesia machine exhaust emission control system
210—Connection pipeline
220—Electronic flow detector
230—Controller
240—Display
250—Alarm
260—Switch
270—Flow regulator
280—Overflow unit
290—Replenishment unit
285—Overflow replenishment unit
300—Exhaust gas recovery system
400—Atmospheric environment

DETAILED DESCRIPTION

In order to make the objectives, technical solutions and advantages of the present disclosure clearer, an anesthesia machine exhaust emission control system and a control method therefor according to the present disclosure will be further described below in detail through embodiments and the accompanying drawings.

It is to be noted that when an element is referred to as being "fixed to" a further element, it may be directly on the further element, or an intermediate element may be present. When an element is considered as being "connected to" a further element, it may be directly connected to the further element, or an intermediate element may be present simultaneously. In contrast, when an element is referred to as being "directly" "on" a further element, no intermediate element is present. The terms "perpendicular", "horizontal", "left" and "right" and similar expressions used herein are for illustrative purposes only. The various objects in the drawings of the embodiments are drawn at a scale convenient for enumeration, rather than at the scale of actual assemblies.

Figure 1:
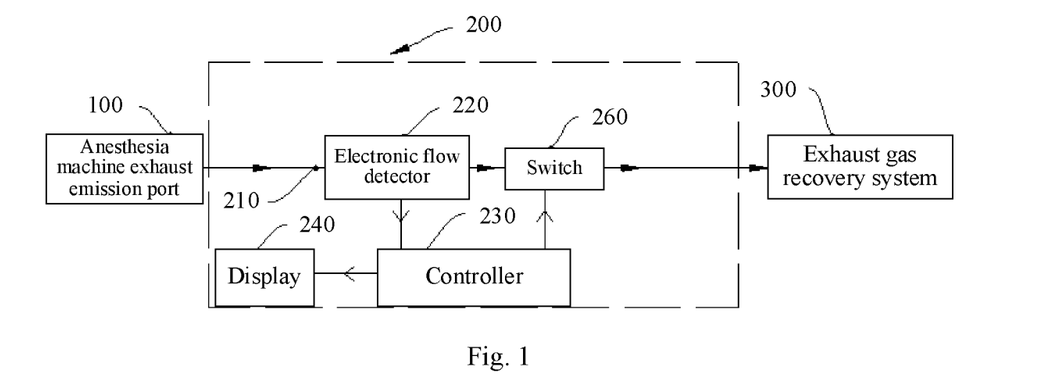
FIG. 1 is a schematic diagram of an anesthesia machine exhaust emission control system provided by a first embodiment of the present disclosure.

As shown in FIG. 1, an embodiment of the present disclosure provides an anesthesia machine exhaust emission control system 200, which is arranged between an exhaust gas recovery system 300 and an anesthesia machine exhaust emission port 100, and includes a connection pipeline 210, an electronic flow detector 220, a controller 230, a display 240 and a switch 260. The connection pipeline 210 includes a gas inlet end and a gas outlet end. The gas inlet end of the connection pipeline 210 is connected to the anesthesia machine exhaust emission port 100, the gas outlet end of the connection pipeline 210 is connected to the exhaust gas recovery system 300, and exhaust gas generated by an anesthesia machine may enter the exhaust gas recovery system 300 through the connection pipeline 210. The electronic flow detector 220 is arranged on the connection pipeline 210, and the electronic flow detector 220 may monitor a gas flow in the connection pipeline 210. The controller 230 is electrically connected to the electronic flow detector 220, and the controller 230 may obtain a gas flow value in the connection pipeline 210 that is monitored by the electronic flow detector 220. The display 240 is electrically connected to the controller 230, and the controller 230 may transmit the gas flow value in the connection pipeline 210 to the display 240 for display. The switch 260 is arranged on the connection pipeline 210, and the switch 260 may open or close the connection pipeline 210. The switch 260 is electrically connected to the controller 230, and the controller 230 may control the switch 260 according to an operating state of the anesthesia machine. When the anesthesia machine is in a ventilation state, the controller 230 controls the switch 260 to open the connection pipeline 210. When the anesthesia machine is in a standby state, the controller 230 controls the switch 260 to close the connection pipeline 210.

In the above-mentioned anesthesia machine exhaust emission control system 200, the gas flow value in the connection pipeline 210 is directly displayed by the electronic flow detector 220, the controller 230 and the display 240; a user may conveniently know the gas flow value in the connection pipeline 210; and the display 240 directly displays the gas flow value in the connection pipeline 210, which greatly improves the accuracy of data read by the user and ensures the smooth progress of an anesthesia process to a certain extent. At the same time, the controller 230 controls the switch 260 to open or close the connection pipeline 210 according to the operating state of the anesthesia machine. When a single or several anesthesia machines are in a standby state, the controller 230 controls the switch 260 to close the corresponding connection pipeline 210, and the hospital exhaust gas recovery system 300 only needs to extract exhaust gas from the anesthesia machine which is discharging the exhaust gas, thereby greatly saving on the hospital exhaust gas recovery resource.

The function of the electronic flow detector 220 used in the present disclosure is to detect the gas flow in the connection pipeline 210, and transmit the monitored data to the controller 230. Optionally, the electronic flow detector 220 used in the present disclosure may be connected in series to the connection pipeline 210, or may be connected to a branch which is connected to the connection pipeline 210, and as long as the function of measuring the gas flow in the connection pipeline 210 may be finally measured, this embodiment does not limit the specific connection of the electronic flow detector 220 and the connection pipeline 210. The electronic flow detector 220 used in the present disclosure may be a detector, such as a rotor flow meter or an electromagnetic flowmeter, which may directly detect the gas flow in the connection pipeline 210. The electronic flow detector 220 used in the present disclosure may also be a detector, such as a pressure sensor or a speed sensor, which indirectly detects the gas flow in the connection pipeline 210 through an intermediate parameter. Optionally, the display 240 used in the present disclosure may be a separate display device, or may be integrated with an existing display device of the anesthesia machine. As long as the gas flow in the connection pipeline 210 that is detected by the electronic flow detector 220 may be displayed under the control of the controller 230, this embodiment does not limit the specific type of the display device.

In one of the particular embodiments, the electronic flow detector 220 may directly detect the gas flow in the connection pipeline 210. Specifically, the electronic flow detector 220 is a rotor flow meter, and the rotor flow meter is directly connected in series to the connection pipeline 210, and may detect the gas flow value in the connection pipeline 210 in real time. At the same time, the rotor flow meter is electrically connected to the controller 230, and the rotor flow meter converts a detected gas flow signal into an electrical signal and transmits same to the controller 230. The controller 230 receives the electrical signal carrying information of the gas flow and also outputs display information to a display screen of the anesthesia machine, and the gas flow in the connection pipeline 210 may be displayed on the display screen of the anesthesia machine. In another particular embodiment, the electronic flow detector 220 is a pressure sensor, the pressure sensor is arranged in the connection pipeline 210, and the pressure sensor outputs a pressure value in the connection pipeline 210 to the controller 230. The controller 230 converts the pressure value detected by the pressure sensor into a gas flow value through a certain calculation, and transmits the converted gas flow value to a separate display screen of the anesthesia machine exhaust emission control system 200 for display.

The switch 260 is provided on the connection pipeline 210, and the controller 230 is used to associate the switch 260 with ventilation and standby states of the anesthesia machine. The on-off of the switch 260 is adjusted in real time according to the operating state of the anesthesia machine, thereby realizing the automatic control of the on-off of the connection pipeline 210. When the anesthesia machine is in the standby state, the switch 260 closes the connection pipeline 210, thereby saving on the recovery resource of the exhaust gas recovery system 300. The function of the switch 260 is to enable the function of opening or closing the connection pipeline 210 under the action of the controller 230. Optionally, the switch 260 provided by the present disclosure may be an electric stop valve, a pneumatic stop valve, an electromagnetic stop valve, or a hydraulically powered slide valve with an on-off function. In one of the particular embodiments, the switch 260 is an electromagnetic stop valve. When the anesthesia machine is in a standby state, the controller 230 controls the electromagnetic stop valve to close the connection pipeline 210. When the anesthesia machine is in a ventilation state, the controller 230 controls the electromagnetic stop valve to open the connection pipeline 210. In another particular embodiment, the switch 260 is a hydraulically powered slide valve with an on-off function. Further, the controller 230 may also control the switch 260 according to the on-off states of the anesthesia machine. When the anesthesia machine is in a power-off state, the controller 230 controls the switch 260 to close the connection pipeline 210. When the anesthesia machine is in the power-off state, the switch 260 closes the connection pipeline 210, thereby further saving on the recovery resource of the exhaust gas recovery system 300.

Figure 2:
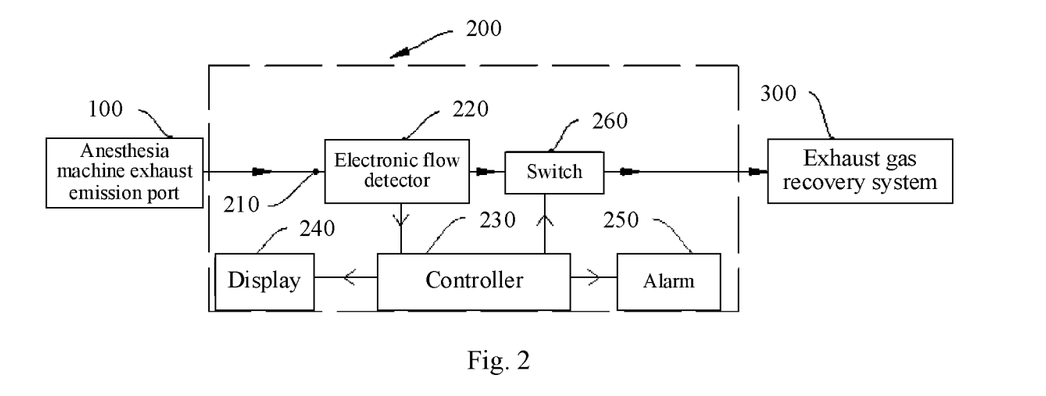
FIG. 2 is a schematic diagram of an anesthesia machine exhaust emission control system provided by a second embodiment of the present disclosure.

In one of the embodiments, as shown in FIG. 2, the anesthesia machine exhaust emission control system 200 provided by the present disclosure further includes an alarm 250. The alarm 250 is electrically connected to the controller 230, and the controller 230 may compare the gas flow value in the connection pipeline 210 with a preset range value.

When the gas flow value in the connection pipeline 210 overflows the preset range value, the controller 230 controls the alarm 250 to send out an alarm signal. The alarm 250 is additionally provided in the anesthesia machine exhaust emission control system 200, and may timely remind the user of the anesthesia machine when the gas flow value in the connection pipeline 210 overflows a set range, so that the user of the anesthesia machine may timely perform the corresponding treatment or remedy. The function of the alarm 250 used in the present disclosure is to send out the alarm signal to draw the attention of the user of the anesthesia machine. Optionally, the alarm 250 may emit a light signal, such as a change in the color of an indicator light, or a set color displayed by the display 240. The alarm 250 may also emit a sound signal, such as a whistle or a language reminder. As long as the user of the anesthesia machine may be timely reminded when the gas flow value in the connection pipeline 210 overflows the set range, this embodiment does not limit the specific type of the alarm 250.

Optionally, the preset range value to be compared with the gas flow value in the connection pipeline 210 may be a range value set each time the anesthesia machine is activated, or a range value that is always stored in the anesthesia machine exhaust emission control system 200. The specific numerical range of the preset range value may refer to one of a national standard, an industrial standard or an enterprise standard, or may be a numerical range designed according to an actual condition. When the user designs the preset range value according to the actual condition, it must also meet at least one of the national standard, the industry standard and the enterprise standard. In one of the particular embodiments, the alarm 250 displays a red background by the display screen of the anesthesia machine. The preset range value is set and stored in the anesthesia machine exhaust emission control system 200 when the device is installed, and the preset range is 25 ml/min-50 ml/min. The electronic flow detector 220 transmits the gas flow value in the connection pipeline 210 to the controller 230. The controller 230 transmits the received gas flow value to the display 240 for display, and also compares the received gas flow value with the preset range value. When gas flow value in the connection pipeline 210 is greater than 50 ml/min or less than 25 ml/min, the controller 230 controls the display screen of the anesthesia machine such that the display screen displays a red background. In another particular embodiment, the alarm 250 is a loudspeaker. When the gas flow value in the connection pipeline 210 is greater than 50 ml/min or less than 25 ml/min, intermittent buzzing may be emitted to remind the user of the anesthesia machine.

Figure 3:
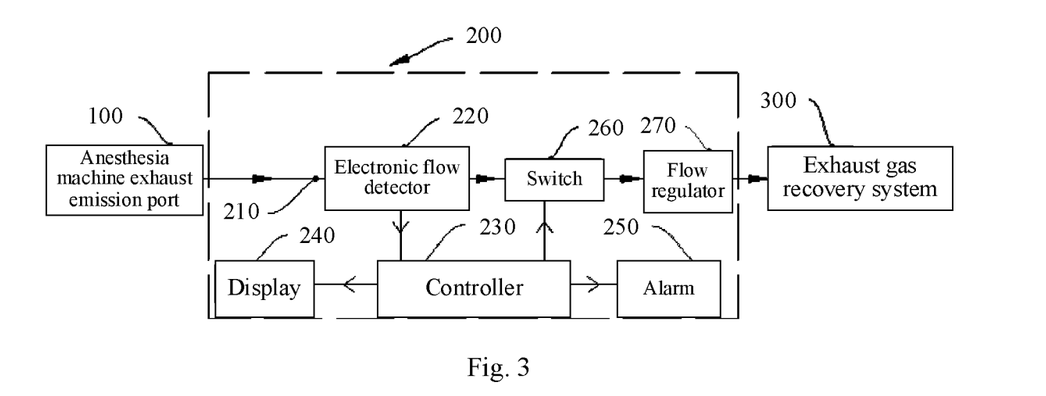
FIG. 3 is a schematic diagram of an anesthesia machine exhaust emission control system provided by a third embodiment of the present disclosure.

In one of the embodiments, as shown in FIG. 3, the anesthesia machine exhaust emission control system 200 further includes a flow regulator 270. The flow regulator 270 may adjust the gas flow in the connection pipeline 210. The flow regulator 270 is arranged on the connection pipeline 210, and may adjust the gas flow in the connection pipeline 210, thereby enhancing the adjustment and control capabilities of the anesthesia machine exhaust emission control system 200 provided by the present disclosure. The function of the flow regulator 270 is to adjust the gas flow in the connection pipeline 210. Optionally, the flow regulator 270 may be a manual flow regulator such as a manual throttle valve, or an automatic flow regulator such as a proportional valve and a servo valve, or a manual flow regulator combined with an automatic flow regulator. As long as the gas flow in the connection pipeline 210 may be controlled, this embodiment does not limit the specific implementation form of the flow regulator 270.

Figure 4:
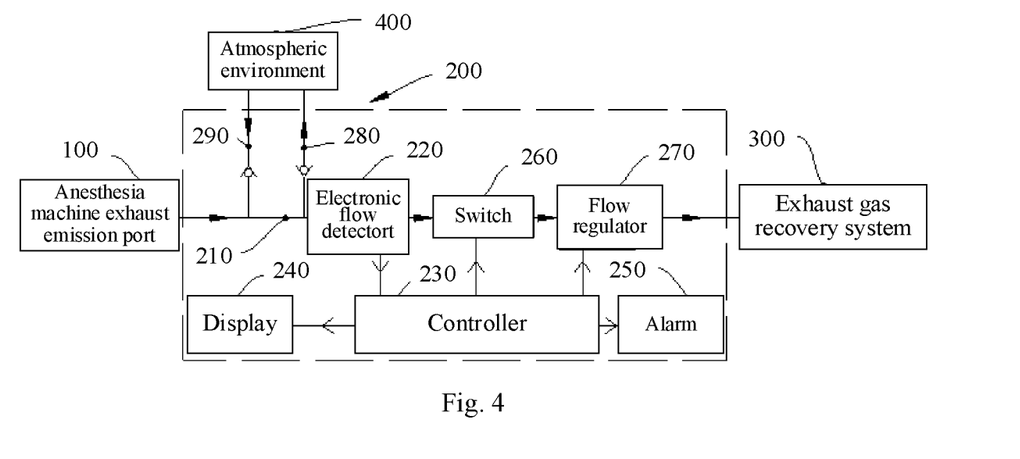
FIG. 4 is a schematic diagram of an anesthesia machine exhaust emission control system provided by a fourth embodiment of the present disclosure.

As shown in FIG. 4, further, the flow regulator 270 is electrically connected to the controller 230. The controller 230 may compare the gas flow value in the connection pipeline 210 with the preset range value. When the gas flow value in the connection pipeline 210 is greater than the maximum value of the preset range value, the controller 230 controls the flow regulator 270 to reduce the flow value allowed to pass through the flow regulator 270. When the gas flow value in the connection pipeline 210 is less than the minimum value of the preset range value, the controller 230 controls the flow regulator 270 to increase the flow value allowed to pass through the flow regulator 270. In a particular embodiment, the flow regulator 270 is an electromagnetic proportional valve, and the electromagnetic proportional valve is electrically connected to the controller 230. The controller 230 uses the display 240 to display the gas flow value in the connection pipeline 210 that is received from the electronic flow detector 220, and at the same time, the controller 230 compares the gas flow value in the connection pipeline 210 with the preset range value. When the gas flow value in the connection pipeline 210 is greater than the maximum value of the preset range value, the controller 230 controls the electromagnetic proportional valve to reduce the flow value allowed to pass through so as to reduce the gas flow in the connection pipeline 210. When the gas flow value in the connection pipeline 210 is less than the minimum value of the preset range value, the controller 230 controls the electromagnetic proportional valve to increase the flow value allowed to pass through. The gas flow in the connection pipeline 210 is automatically controlled in real time. The user of the anesthesia machine does not need to give consideration on the task of adjusting the gas flow in the connection pipeline 210, which reduces the possibility of misoperation. In another particular embodiment, the flow regulator 270 is used when the manual throttle valve and the electromagnetic proportional valve are connected in series. Generally, the manual throttle valve is at the maximum flow state, and the electromagnetic proportional valve electrically connected to the controller 230 has the function of adjusting the gas flow in the connection pipeline 210. When the electromagnetic proportional valve is not capable of adjusting, the user of the anesthesia machine may also adjust the gas flow in the connection pipeline 210 by the manual throttle valve.

In one of the embodiments, as shown in FIG. 4, the anesthesia machine exhaust emission control system 200 further includes an overflow unit 280. The overflow unit 280 is in communication with one end of the connection pipeline 210 which is close to the anesthesia machine exhaust emission port 100. When the amount of exhaust gas actually discharged from the anesthesia machine is greater than a gas extraction flow of the exhaust gas recovery system 300, excess exhaust gas is discharged from the overflow unit 280. In a particular embodiment, the overflow unit includes an overflow pipeline and an overflow one-way valve. One end of the overflow pipeline is in communication with one end of the connection pipeline 210 which is close to the anesthesia machine exhaust emission port 100, the other end of the overflow pipeline is in communication with the external atmospheric environment 400, and the overflow one-way valve is connected in series to the overflow pipeline. In another embodiment, the overflow unit 280 may also be an overflow one-way switch provided on the surface of the connection pipeline 210. When the amount of exhaust gas actually discharged from the anesthesia machine is greater than a gas extraction flow of the exhaust gas recovery system 300, excess exhaust gas is discharged from the overflow one-way switch, to ensure smooth discharge of exhaust gas generated by the anesthesia machine.

In one of the embodiments, as shown in FIG. 4, the anesthesia machine exhaust emission control system 200 further includes a replenishment unit 290. The replenishment unit 290 is in communication with one end of the connection pipeline 210 which is close to the anesthesia machine exhaust emission port 100, and when the amount of exhaust gas actually discharged from the anesthesia machine is less than a gas extraction flow of the exhaust gas recovery system 300, gas in the environment may enter the connection pipeline 210 from the replenishment unit 290. In a particular embodiment, the replenishment unit includes a replenishment pipeline and a replenishment one-way valve. One end of the replenishment pipeline is in communication with one end of the connection pipeline 210 which is close to the anesthesia machine exhaust emission port 100, the other end of the replenishment pipeline is in communication with the external atmospheric environment 400, and the replenishment one-way valve is connected in series to the replenishment pipeline. In another embodiment, the replenishment unit 290 may also be a replenishment one-way switch provided on the surface of the connection pipeline 210. When the amount of exhaust gas actually discharged from the anesthesia machine is less than a gas extraction flow of the exhaust gas recovery system 300, gas in the environment may enter the connection pipeline 210 from the replenishment one-way switch, to ensure a normal gas pressure in the anesthesia machine.

Figure 5:
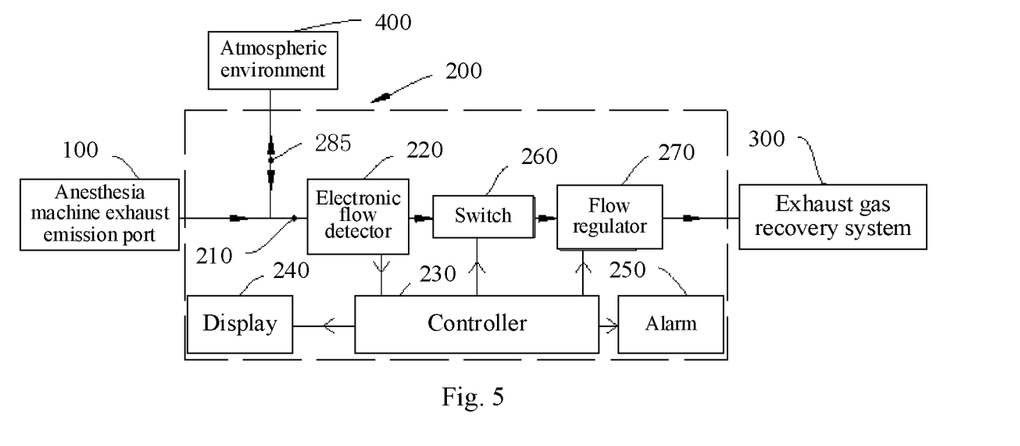
FIG. 5 is a schematic diagram of an anesthesia machine exhaust emission control system provided by a fifth embodiment of the present disclosure.

As shown in FIG. 5, in a particular embodiment, the overflow unit 280 and the replenishment unit 290 are combined into an overflow replenishment unit 285, and the overflow pipeline and the replenishment pipeline are combined into an overflow replenishment pipeline. In this case, exhaust gas is discharged into the atmospheric environment 400 through the overflow replenishment pipeline, and the ambient gas in the atmospheric environment 400 may also enter the connection pipeline 210 from the overflow replenishment pipeline and then enter the exhaust gas recovery system 300. In addition, when the exhaust gas recovery system 300 fails and the exhaust gas may not be discharged actively, the method of passive exhaust may be used, so that the exhaust gas generated by the anesthesia machine is discharged to the atmospheric environment 400 through the overflow replenishment pipeline, so as to ensure the normal operation of the anesthesia machine, and thus to ensure the smooth progress of the operation.

One embodiment of the present disclosure further provides an anesthesia machine exhaust emission control method, which includes:
  obtaining an exhaust emission flow of an anesthesia machine;
  displaying the exhaust emission flow of the anesthesia machine; and
  obtaining an operating state of the anesthesia machine, and opening or closing an exhaust passage between an anesthesia machine exhaust emission port 100 and an exhaust gas recovery system 300 according to the operating state of the anesthesia machine. When the anesthesia machine is in a ventilation state, the exhaust passage between the anesthesia machine exhaust emission port 100 and the exhaust gas recovery system 300 is opened. When the anesthesia machine is in a standby state, the exhaust passage between the anesthesia machine exhaust emission port 100 and the exhaust gas recovery system 300 is closed.

In the above-mentioned anesthesia machine exhaust emission control method, obtaining and displaying the exhaust emission flow of the anesthesia machine is convenient for a user of the anesthesia machine to know an exhaust emission parameter of the anesthesia machine more conveniently. The on-off of the exhaust passage is adjusted in real time according to the operating state of the anesthesia machine, thereby realizing the automatic control of the on-off of the exhaust passage. The exhaust passage is closed when the anesthesia machine is in the standby state, which saves on the recovery resource of the exhaust gas recovery system 300.

Further, the process of obtaining the exhaust emission flow of the anesthesia machine and displaying the exhaust emission flow of the anesthesia machine may be detected and displayed by a mechanical flow detector, or may be detected by the electronic flow detector 220 and then displayed by an external display 240. This embodiment does not limit the specific method of obtaining the exhaust emission flow of the anesthesia machine and displaying the exhaust emission flow of the anesthesia machine.

In one of the embodiments, the anesthesia machine exhaust emission control method further includes:
  comparing the obtained exhaust emission flow of the anesthesia machine with a preset range value; and
  if the exhaust emission flow of the anesthesia machine is greater than the maximum value of the preset range value or less than the minimum value of the preset range value, sending out an alarm signal by an alarm 250.

Further, in this embodiment, the exhaust emission flow of the anesthesia machine is detected by the electronic flow detector 220. The alarm signal sent by the alarm 250 may be an image, a sound, or any other signal serving as a reminder. In a particular embodiment, the exhaust emission flow of the anesthesia machine is detected by the electronic flow detector 220, and then the obtained exhaust emission flow of the anesthesia machine is compared with the preset range value. If the exhaust emission flow of the anesthesia machine is greater than the maximum value of the preset range value or less than the minimum value of the preset range value, an alarm 250 emits intermittent buzzing.

In one of the embodiments, the anesthesia machine exhaust emission control method further includes:
  obtaining the on-off state of the anesthesia machine; and
  if the anesthesia machine is in a power-off state, closing the exhaust passage between the anesthesia machine and the exhaust gas recovery system 300. The exhaust passage is closed when the anesthesia machine is in the power-off state, which further saves on the recovery resource of the exhaust gas recovery system 300.

The various technical features of the embodiments described above may be arbitrarily combined. In order to simplify the description, all possible combinations of the various technical features in the above embodiments have not been described. However, any combination of these technical features should be considered to fall with the scope of the disclosure of this description as long as there is no contradiction.

The above-mentioned embodiments merely represent several implementations of the present disclosure, giving specifics and details thereof, but should not be understood as limiting the scope of the present patent of disclosure thereby. It should be noted that a person of ordinary skill in the art could also make several variations and improvements without departing from the concept of the present disclosure. These variations and improvements all fall within the scope of protection of the present disclosure. Therefore, the scope of protection of the present patent of invention shall be in accordance with the appended claims.

What is claimed is:

1. An anesthesia machine exhaust emission control system, which is arranged between an exhaust gas recovery system and an anesthesia machine exhaust emission port, comprising:
   a connection pipeline comprising a gas inlet end and a gas outlet end, wherein the gas inlet end of the connection pipeline is connected to the anesthesia machine exhaust emission port, the gas outlet end of the connection pipeline is connected to the exhaust gas recovery system, and exhaust gas generated by the anesthesia machine is capable of entering the exhaust gas recovery system through the connection pipeline;
   an electronic flow detector arranged on the connection pipeline, wherein the electronic flow detector is configured to monitor a gas flow in the connection pipeline;
   a controller electrically connected to the electronic flow detector, wherein the controller is configured to obtain a gas flow value in the connection pipeline that is monitored by the electronic flow detector;
   a display electrically connected to the controller, wherein the controller is further configured to transmit the gas flow value in the connection pipeline to the display for display; and
   a switch arranged at the connection pipeline, wherein the switch is configured to open or close the connection pipeline, the switch is electrically connected to the controller, wherein the controller is further configured to obtain an operating state of the anesthesia machine, and control the switch to automatically switch on or off in real time in response to a change of the operating state of the anesthesia machine when the anesthesia machine is in a power on state, wherein the operating state of the anesthesia machine comprises a ventilation state in which the exhaust gas is generated and a standby state in which the exhaust gas is not generated, when the anesthesia machine is in the ventilation state, the controller is configured to control the switch to open the connection pipeline to the exhaust gas recovery system, and when the anesthesia machine is in the standby state, the controller is configured to control the switch to close the connection pipeline to the exhaust gas recovery system in order to avoid exhaust gas recovery system extracting a large amount of air from the anesthesia machine in the standby state.

2. The anesthesia machine exhaust emission control system of claim 1, further comprising an alarm, wherein the alarm is electrically connected to the controller,
   wherein the controller is further configured to compare the gas flow value in the connection pipeline with a preset range value,
   wherein when the gas flow value in the connection pipeline overflows the preset range value, the controller is configured to control the alarm to send out an alarm signal.

3. The anesthesia machine exhaust emission control system of claim 1, wherein the controller is further configured to control the switch according to the on-off state of the anesthesia machine,
   wherein when the anesthesia machine is in a power-off state, the controller is configured to control the switch to close the connection pipeline.

4. The anesthesia machine exhaust emission control system of claim 1, further comprising a flow regulator, wherein the flow regulator is configured to adjust the gas flow in the connection pipeline.

5. The anesthesia machine exhaust emission control system of claim 4, wherein the flow regulator is electrically connected to the controller, wherein the controller is configured to compare the gas flow value in the connection pipeline with a preset range value,
   wherein when the gas flow value in the connection pipeline is greater than the maximum value of the preset range value, the controller is configured to control the flow regulator to reduce the flow value allowed to pass through the flow regulator, and
   wherein when the gas flow value in the connection pipeline is less than the minimum value of the preset range value, the controller is configured to control the flow regulator to increase the flow value allowed to pass through the flow regulator.

6. The anesthesia machine exhaust emission control system of claim 1, further comprising an overflow unit, wherein the overflow unit is in communication with one end of the connection pipeline which is close to the anesthesia machine exhaust emission port,
   wherein when the amount of exhaust gas actually discharged from the anesthesia machine is greater than a gas extraction flow of the exhaust gas recovery system, excess exhaust gas is discharged from the overflow unit.

7. The anesthesia machine exhaust emission control system of claim 1, further comprising a replenishment unit, wherein the replenishment unit is in communication with one end of the connection pipeline which is close to the anesthesia machine exhaust emission port,
   wherein when the amount of exhaust gas actually discharged from the anesthesia machine is less than a gas extraction flow of the exhaust gas recovery system, gas in the environment is capable of entering the connection pipeline from the replenishment unit.

8. An anesthesia machine exhaust emission control system, which is arranged between an exhaust gas recovery system and an anesthesia machine exhaust emission port, comprising:
   a connection pipeline comprising a gas inlet end and a gas outlet end, wherein the gas inlet end of the connection pipeline is connected to the anesthesia machine exhaust emission port, the gas outlet end of the connection pipeline is connected to the exhaust gas recovery system, and exhaust gas generated by the anesthesia machine is capable of entering the exhaust gas recovery system through the connection pipeline;
   an electronic flow detector arranged on the connection pipeline, wherein the electronic flow detector is configured to monitor a gas flow in the connection pipeline;
   a controller electrically connected to the electronic flow detector, wherein the controller is configured to obtain a gas flow value in the connection pipeline that is monitored by the electronic flow detector;
   a display electrically connected to the controller, wherein the controller is further configured to transmit the gas flow value in the connection pipeline to the display for display; and
   a switch arranged at the connection pipeline, wherein the switch is configured to open or close the connection pipeline, the switch is electrically connected to the controller, wherein the controller is further configured to obtain an on-off state of the anesthesia machine, and control the switch the on-off state of the anesthesia machine, and wherein when the anesthesia machine is in a power-on state, the controller is configured to control the switch to open the connection pipeline, wherein when the anesthesia machine is in a power-off state, the controller is configured to control the switch to close the connection pipeline, wherein the controller is further configured to obtain an operating state of the anesthesia machine, and control the switch to automatically switch on or off in real time in response to a change of the operating state of the anesthesia machine when the anesthesia machine is in a power on state, wherein when the anesthesia machine is in a standby state wherein the exhaust gas is not generated, the controller is configured to control the switch to close the connection pipeline to the exhaust gas recovery system in order to avoid exhaust gas recovery system extracting a large amount of air from the anesthesia machine in the standby state.

9. The anesthesia machine exhaust emission control system of claim 8, further comprising an alarm, wherein the alarm is electrically connected to the controller, wherein the controller is further configured to compare the gas flow value in the connection pipeline with a preset range value, and wherein when the gas flow value in the connection pipeline overflows the preset range value, the controller controls the alarm to send out an alarm signal.

10. The anesthesia machine exhaust emission control system of claim 8, further comprising a flow regulator, wherein the flow regulator is configured to adjust the gas flow in the connection pipeline.

11. The anesthesia machine exhaust emission control system of claim 10, wherein the flow regulator is electrically connected to the controller, wherein the controller is configured to compare the gas flow value in the connection pipeline with a preset range value,
   wherein when the gas flow value in the connection pipeline is greater than the maximum value of the preset range value, the controller is configured to control the flow regulator to reduce the flow value allowed to pass through the flow regulator,
   wherein when the gas flow value in the connection pipeline is less than the minimum value of the preset range value, the controller is configured to control the flow regulator to increase the flow value allowed to pass through the flow regulator.

12. The anesthesia machine exhaust emission control system of claim 8, further comprising an overflow unit, wherein the overflow unit is in communication with one end of the connection pipeline which is close to the anesthesia machine exhaust emission port,
   wherein when the amount of exhaust gas actually discharged from the anesthesia machine is greater than a gas extraction flow of the exhaust gas recovery system, excess exhaust gas is discharged from the overflow unit.

13. The anesthesia machine exhaust emission control system of claim 8, further comprising a replenishment unit, wherein the replenishment unit is in communication with one end of the connection pipeline which is close to the anesthesia machine exhaust emission port,
   wherein when the amount of exhaust gas actually discharged from the anesthesia machine is less than a gas extraction flow of the exhaust gas recovery system, gas in the environment is capable of entering the connection pipeline from the replenishment unit.

14. An anesthesia machine exhaust emission control method, comprising:
   obtaining an operating state of the anesthesia machine; and
   associating a switch with the operating state, wherein the switch automatically switches on or off in real time in response to a change of the operating state when the anesthesia machine is in a power on state to open or close an exhaust passage between an anesthesia machine exhaust emission port and an exhaust gas recovery system according to the operating state of the anesthesia machine, comprising:
   when the anesthesia machine is in a ventilation state wherein the exhaust gas is generated, controlling the switch to open the exhaust passage between the anesthesia machine exhaust emission port and the exhaust gas recovery system,
   wherein when the anesthesia machine is in a standby state wherein the exhaust gas is not generated, controlling the switch to close the exhaust passage between the anesthesia machine exhaust emission port and the exhaust gas recovery system in order to avoid exhaust gas recovery system extracting a large amount of air from the anesthesia machine in the standby state.

15. The anesthesia machine exhaust emission control method of claim 14, further comprising:
   obtaining an exhaust emission flow of the anesthesia machine; and
   displaying the exhaust emission flow of the anesthesia machine.

16. The anesthesia machine exhaust emission control method of claim 15, further comprising:
   comparing the obtained exhaust emission flow of the anesthesia machine with a preset range value; and
   if the exhaust emission flow of the anesthesia machine is greater than the maximum value of the preset range value or less than the minimum value of the preset range value, sending out an alarm signal by an alarm.

17. The anesthesia machine exhaust emission control method of claim 15, further comprising:
   comparing the obtained exhaust emission flow of the anesthesia machine with a preset range value;
   when the exhaust emission flow value is greater than the maximum value of the preset range value, controlling a flow regulator to reduce the flow value allowed to pass through the flow regulator; and
   when the exhaust emission flow value is less than the minimum value of the preset range value, controlling the flow regulator to increase the flow value allowed to pass through the flow regulator.

18. The anesthesia machine exhaust emission control method of claim 14, further comprising:
   obtaining an on-off state of the anesthesia machine; and
   if the anesthesia machine is in a power-off state, closing the exhaust passage between the anesthesia machine and the exhaust gas recovery system.

19. The anesthesia machine exhaust emission control method of claim 14, further comprising:
   controlling an overflow unit to discharge excess exhaust gas when the amount of exhaust gas actually discharged from the anesthesia machine is greater than a gas extraction flow of the exhaust gas recovery system.

20. The anesthesia machine exhaust emission control method of claim 14, further comprising:
   controlling gas in the environment to enter the exhaust passage from a replenishment unit when the amount of exhaust gas actually discharged from the anesthesia machine is less than a gas extraction flow of the exhaust gas recovery system.

\* \* \* \* \*